United States Patent [19]

Nachbur

[11] Patent Number: 4,754,063
[45] Date of Patent: Jun. 28, 1988

[54] SALICYLATES AND PROCESS FOR THEIR PREPARATION

[75] Inventor: Hermann Nachbur, Reinach, Switzerland

[73] Assignee: Ciba-Geigy Corporation, Ardsley, N.Y.

[21] Appl. No.: 51,782

[22] Filed: May 20, 1987

Related U.S. Application Data

[62] Division of Ser. No. 786,458, Oct. 11, 1985, Pat. No. 4,687,869.

[30] Foreign Application Priority Data

Oct. 22, 1984 [CH] Switzerland ............... 5046/84

[51] Int. Cl.$^4$ ............................. C07G 69/76
[52] U.S. Cl. ................................. 562/468
[58] Field of Search ............. 562/468; 560/57

[56] References Cited

U.S. PATENT DOCUMENTS 3,215,722  11/1965  Turk ................... 562/468
3,923,828  12/1975  Williams ............ 562/468
3,957,862   5/1976  Heath ................. 562/468

Primary Examiner—Paul J. Killos
Attorney, Agent, or Firm—Edward McC. Roberts; Meredith C. Findlay

[57] ABSTRACT

The invention relates to metal salicylates of the formula

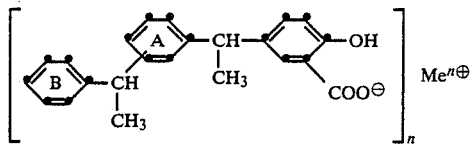

wherein
Me is a metal ion of valency n,
n is 2, 3 or 4, and
each of the rings A and B independently of the other is unsubstituted or substituted by halogen, lower alkyl, lower alkoxy or an α-methylbenzyl radical.

The metal salicylates are particularly suitable developers for the color former in pressure-sensitive or heat-sensitive recording materials.

5 Claims, No Drawings

SALICYLATES AND PROCESS FOR THEIR PREPARATION

This is a divisional of application Ser. No. 786,458 filed on Oct. 11, 1985, now U.S. Pat. No. 4,687,869, issued on Aug. 18, 1987.

The present invention relates to metal salicylates, to a process for the preparation thereof, and to the use of these compounds in pressure-sensitive and heat-sensitive recording materials. The metal salicylates have the formula

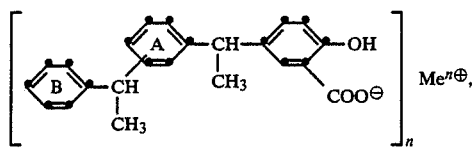 (1)

wherein
Me is a metal ion of valency n,
n is 2, 3 or 4, and
each of the rings A and B independently of the other is unsubstituted or substituted by halogen, lower alkyl, lower alkoxy or an α-methylbenzyl radical.

The salicylate moieties occurring 2 to 4 times in the above metal salts may be identical or different. Preferably they are all identical.

Lower alkyl and lower alkoxy normally denote groups containing 1 to 5, preferably 1 to 3, carbon atoms. Lower alkyl groups may be methyl, ethyl, isopropyl, sec-butyl, tert-butyl, amyl or isoamyl, and lower alkoxy groups may be methoxy, ethoxy, isopropoxy, n-butoxy or tert-butoxy.

Halogen in the definition of formula (1) denotes for example fluorine, iodine, bromine or, preferably, chlorine.

The metal salts of this invention are preferably derived from divalent, trivalent or quadrivalent metals having an atomic weight from 24 to 210, preferably from 26 to 120. Examples of such metals are aluminium, barium, lead, cadmium, calcium, chromium, iron, gallium, cobalt, copper, magnesium, manganese, molybdenum, nickel, mercury, silver, strontium, tantalum, titanium, vanadium, tungsten, zinc, tin and zirconium. Preferred metals are aluminium, titanium, vanadium, tin and, in particular, zinc. The

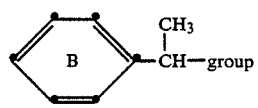

is preferably para to the ethylidene group. The rings A and B are preferably not further substituted. If they do contain substituents, then they are preferably further substituted by halogen, methyl, methoxy or α-methylbenzyl. Each benzene ring A and B may conveniently contain 1 or 2 additional substituents. The α-methylbenzyl radical is normally present in the ring B.

Interesting developers which may be used with advantage in the practice of this invention, and which may be obtained by the methods described hereinafter, are aluminium salts or, preferably, zinc salts of a substituted salicyclic acid compound of the formula

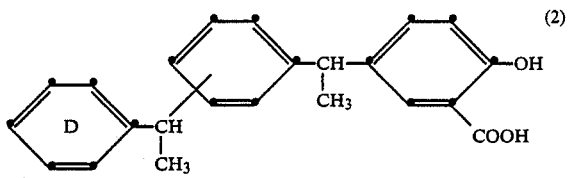 (2)

wherein the ring D is unsubstituted or substituted by α-methylbenzyl.

Among the salicylic acid compounds of formula (2), those compounds are preferred in which the ring D is unsubstituted.

The preferred developer is the zinc salt of 5-[α-methyl-4'-(α-methylbenzyl)benzyl]salicylic acid.

The metal compounds of formula (1) constitute a novel class of metal salts which are suitable developers or electron acceptors for electron-releasing colour formers.

The metal salicylates of formula (1) are prepared by reacting 1 mole of a salt of an n-valent metal of an inorganic acid or of a lower aliphatic carboxylic acid with n moles of a salicylic acid compound of the formula

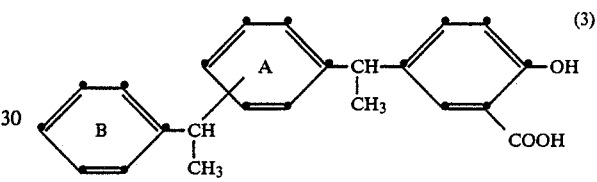 (3)

wherein n, A and B have the given meanings.

The reaction is conveniently carried out in an alkaline solution of the salicyclic acid compound and preferably in the presence of an alkali, for example a hydroxide, carbonate or bicarbonate of an alkali metal, or ammonium hydroxide, ammonium carbonate or ammonium bicarbonate.

The metallisation can be carried out in the temperature range from 10° to 25° C. In certain cases, and especially when using organic aluminium salts, it is necessary to carry out the reaction at elevated temperature, preferably in the range from 70° to 200° C. However, the reactants can also be reacted in a melt. Suitable fusing assistants are for example salts of lower fatty acids, e.g. sodium acetate, amides of lower fatty acids, e.g. acetamide, and also urea or thiourea or N-substitution products thereof.

As metal donors it is convenient to use the metal salts of mineral acids or carboxylic acids of 1 to 6 carbon atoms, in particular sulfates, halides (chlorides), nitrates, formates, acetates, propionates, oxalates or citrates.

Representative examples of inorganic metal salts are zinc salts such as zinc chloride, zinc sulfate or zinc nitrate, as well as aluminium sulfate. Examples of organic metal salts are zinc diacetate, zinc oxalate, aluminium triisopropylate or aluminium sec-butylate.

Instead of the above zinc salts, it is also possible to use zinc oxide or zinc carbonate, in which case the reaction with the salicylic acid is preferably carried out in the presence of ammonium formate.

The substituted salicylic acid compounds of formula (3) and the preparation thereof are novel.

The process for their preparation comprises reacting 1 mole of salicylic acid with at least 1 mole of a 1-phenylethanol of the formula

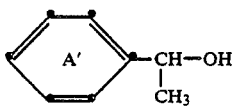

and at least 1 mole of a 1-phenylethanol of the formula

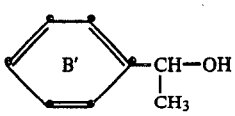

in which formulae (4) and (5) above the rings A' and B' are unsubstituted or substituted by halogen, lower alkyl or lower alkoxy.

The ethanol components of formulae (4) and (5) are preferably identical.

Representative examples of suitable 1-phenylethanol components of formulae (4) and (5) are: 1-phenylethanol, 1-tolylethanol, 1-xylylethanol or 1-(chlorophenyl)ethanol.

The process for the preparation of the salicylic acid compounds of formula (3) is conveniently carried out in an organic solvent which does not participate in the condensation and in the presence of an acid catalyst, in the temperature range from 20° C. to the reflux temperature of the reaction medium, preferably from 80° to 150° C. The reaction time depends on the temperature and is ordinarily from ½ hour to 5 hours, preferably from 1 to 3 hours.

Suitable organic solvents employed as reaction medium are cycloaliphatic or, preferably, aromatic hydrocarbons, for example cyclohexane, benzene, toluene or xylene; chlorinated hydrocarbons such as ethylene chloride, tetrachloroethylene, or chlorobenzenes, e.g. chlorobenzene, chlorotoluene or dichlorobenzene; cyclic ethers, e.g. dioxane or tetrahydrofuran; dimethylsulfoxide, or nitriles of aliphatic monocarboxylic acids, e.g. acetonitrile, propionitrile or butyronitrile. Mixtures of these solvents can also be used. Preferred solvents are chlorobenzene, chlorotoluene and, in particular, toluene.

Suitable acid catalysts are aromatic sulfonic acids, e.g. benzenesulfonic acid, chlorobenzenesulfonic acid, toluenesulfonic acid, chlorotoluenesulfonic acid or xylenesulfonic acid.

Aromatic sulfonic acids which are formed in situ are preferred, with toluenesulfonic acid being especially preferred. The preparation of toluenesulfonic acid in situ is described e.g. in Chemical Abstracts, Vol. 79 (1969), 1066228r. p-Toluenesulfonic acid is also preferred. If this last mentioned compound is used, a solvent may be dispensed with.

After the condensation of the salicylic acid with the other starting materials of formulae (4) and (5), the substituted salicylic acid of formula (3) can be further used direct for the preparation of the metal salt of formula (1). It it is desired to isolate the substituted salicyclic acid of formula (3), then the acid solution of the reaction product is e.g. first neutralised with aqueous sodium hydroxide solution, and then the neutral solution is acidified with a lower carboxylic acid or an inorganic acid, whereupon the product precipitates in the form of an oil and is separated.

A particularly preferred process for the preparation of the metal compounds of formula (1), wherein Me is the zinc ion, comprises heating to the boil, in a reaction medium consisting of toluene and toluenesulfonic acid prepared in situ, about 1 mole, preferably 1.0 to 1.2 moles, of salicyclic acid with more than 2 moles of 1-phenylethanol and effecting condensation, under reflux temperature, for ½ hour to 2½ hours. The toluene is then removed, the resultant salicylic acid compound of formula (3) is dissolved in an aqueous solution of sodium hydroxide, and the alkaline solution is treated with an inorganic zinc salt, preferably zinc chloride, whereupon the zinc salt of the salicyclic acid compound of formula (3) is isolated.

The metal-free salicylic acid compound can be readily obtained again by dissolving the zinc salt in a polar organic solvent, e.g. acetone, and acidifying the solution with a dilute inorganic acid, e.g. hydrochloric acid.

A meterial advantage of the present invention resides in the feature that, surprisingly, by suitable choice of starting materials, in particular salicylic acid and 1-phenylethanol, it is possible to obtain a novel readily accessible ring-substituted salicylic acid compound instead of an esterification product of the salicylic acid, the metal salt, especially the zinc salt, of which compound is an excellent and economically interesting developer for colour formers for use in pressure-sensitive as well as heat-sensitive recording materials.

The metal salicylates of the formula (1) are virtually colourless and odourless and react very readily with conventional colour formers, so that spontaneous stable and non-fading copies are obtained.

The colour formers suitable for use in the recording or copying material of this invention are known colourless or faintly coloured chromogenic compounds which, on coming into contact with the metal compounds of the formula (1) become coloured or change colour. It is possible to use colour formers, or mixtures thereof, which belong to e.g. the classes of the azomethines, fluoranes, benzofluoranes, phthalides, azaphthalides, spiropyranes, spirodipyranes, leucoauramines, quinazolines, triarylmethaneleuco dyes, carbazolylmethanes, chromenoindoles, rhodamine lactams, chromenopyrazoles, phenoxazines, phenothiazines, as well as chromeno or chromano colour formers.

Examples of such suitable colour formers are: crystal violet lactone (Registered Trademark), 3,3-(bisaminophenyl)phthalides, 3,3-(bis-substituted indolyl)phthalides, 3-(aminophenyl)-3-indolylphthalides, 3-(aminophenyl)-3-indolylazaphthalides, 6-dialkylamino-2-n-octylaminofluoranes, 6-dialkylamino-2-arylaminofluoranes, e.g. 6-diethylamino-2-(2'-chlorophenylamino)-fluorane, 6-dibutylamino-2-(2'-chlorophenylamino)fluorane; 6-dialkylamino-3-methyl-2-arylaminofluoranes, e.g. 2-anilino-3-methyl-6-diethylaminofluorane or 2-(2',4'-dimethylanilino)-3-methyl-6-diethylaminofluorane, 6-dialkylamino-2- or -3-lower alkylfluoranes, 6-dialkylamino-2-dibenzylaminofluoranes, 6-pyrrolidino-2-dibenzylaminofluorane, 6-N-cyclohexyl-N-lower alkyl-3-methyl-2-arylaminofluoranes, 6-pyrrolidino-2-arylaminofluoranes, bis(aminophenyl)furyl-, -phenyl- or -carbazolylmethanes, 3'-phenyl-7-dialkylamino-2',2'-spirodibenzopyranes, bisdialkylaminobenzhydrolalkyl- or -arylsulfinates, benzoyldialkylaminophenothiazines or benzoyldialkylaminophenoxazines.

The metal salicylates of formula (1) are suitable developers for a pressure-sensitive or heat-sensitive recording material which may also be a copying material.

A pressure-sensitive material comprises e.g. at least one pair of sheets which contain at least one colour former, dissolved in an organic solvent, and a metal salicylate of formula (1) as developer.

The developer is preferably applied in the form of a layer to the face of the receiver sheet.

The metal salicylates of formula (1) may be applied by themselves alone, as mixtures or in admixture with known developers. Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay, or acidic organic compounds, for example unsubstituted or ring-substituted phenols, 3,5-bis($\alpha,\alpha$-dimethylbenzyl)salicylic acid, 3,5-bis($\alpha$-methylbenzyl)salicylic acid, or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene.

The developers may also be used in admixture with other basically inert or almost inert pigments or with other auxiliaries such as silica gel or UV absorbers, e.g. 2-(2-hydroxyphenyl)benzotriazoles. Examples of such pigments are: talcum, titanium dioxide, zinc oxide, chalk; clays such as kaolin, as well as organic pigments, e.g. urea/formaldehyde condensates (BET surface area: 2–75 $m^2/g$) or melamine/formaldehyde condensates.

The colour former effects a coloured marking at those points where it comes into contact with the developer. In order to prevent the colour formers contained in the pressure-sensitive recording material from becoming active prematurely, they are usually separated from the developer. This separation can conveniently be accomplished by incorporating the colour formers in foamlike, spongelike or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with the metal salicylate of formula (1) and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g with isopropyl, isobutyl, sec- or tert-butyl) derivative of diphenyl, diphenylalkane, naphthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsules walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specifications Nos. 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

In combination with the developers, the microcapsules containing the colour formers can be used for the production of a wide variety of known kinds of pressure-sensitive copying material. The various systems differ substantially from one another in the arrangement of the capsules, of the colour reactants, i.e. of the developers, and of the support. A preferred arrangement is that in which the encapsulated colour former is in the form of a layer on the back of a transfer sheet and the developer of formula (1) is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The metal compounds of formula (1) can also be employed as developers in a thermoreactive recording material. This recording material usually contains at least one carrier, one colour former, one developer, and optionally also a binder and/or wax.

Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) information can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer.

Another possibility comprises dispersing both the colour former and the developer in one layer. By means of heat the binder is softened at specific areas and the colour former comes into contact with the developer (electron acceptor) at those points where heat is applied and the desired colour develops at once.

Known developers for this purpose are the same developers as are used in pressure-sensitive papers, and also phenolic compounds, for example 4-tert-butylphenol, 4-phenylphenol, methylene bis-(2-methylphenol), 4-hydroxydiphenyl ether, α-naphthol, β-naphthol, methyl, ethyl, n-butyl or benzyl 4-hydroxybenzoate, 4-hydroxyacetophenone, 2,2'-dihydroxydiphenyl, 4,4'-isopropylidenediphenol, 4,4'-isopropylidene-bis(2-methylphenol), 4-hydroxydiphenylsulfone, 4'-methyl-4-hydroxydiphenylsulfone, 2,4-dihydroxydiphenylsulfone, 4,4'-bis(hydroxyphenyl) valeric acid, 2,4-dihydroxybenzophenone, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further auxiliaries. To improve the degree of whiteness, to facilitate the printing of papers, and to prevent the heated pen from sticking, the coatings may contain e.g. talcum, titanium dioxide, zinc oxide, aluminium oxide, aluminium hydroxide, calcium carbonate (e.g. chalk), clays or also organic pigments, for example urea/formaldehyde or melamine/formaldehyde polymers. In order to effect the colour formation only within a limited temperature range, it is possible to add substances such as urea, thiourea, diphenyl thiourea, acetamide, acetanilide, stearylamide, dimethyl terephthalate, phthalic anhydride, metal chlorides, metal stearates, e.g. zinc stereate, phthalonitrile or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

The invention is illustrated by the following Preparatory and Use Examples, in which parts and percentages are by weight, unless otherwise indicated.

PREPARATORY EXAMPLES

Examples 1

250 g of toluene are heated under reflux. Then 7.3 g of 96% sulfuric acid are added dropwise over 50 to 60 minutes and the water formed is removed as an azeotrope. The mixture is then cooled to 60° C. and 250 g of 1-phenylethanol and 155 g of salicylic acid are added. The mixture is heated to reflux temperature and the water formed during the condensation is continuously removed as an azeotrope. The toluene is then removed by distillation and the residue is stirred in 1190 ml of an aqueous 1N sodium hydroxide solution. The resultant solution is allowed to stand for several hours at room temperature, after which time the oil that has formed on the surface is separated. The residual solution is then added dropwise, with efficient stirring, at 10°-15° C. to a solution of 200 g of zinc chloride in 600 ml of water. The white precipitate is isolated by filtration and dissolved in 1 kg of toluene. The toluene solution is concentrated by evaporation at 60° C. under reduced pressure, affording 233 g of an anhydrous powder, which is the zinc salt of the formula

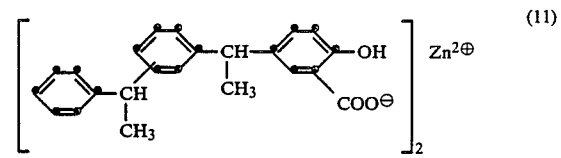

with a melting point of 130°-190° C.

| | Elemental analysis: | | | |
|---|---|---|---|---|
| cal. | C = 73.06% | H = 5.6% | O = 12.7% | Zn = 8.64% |
| found | C = 71.8% | H = 5.7% | O = 12.8% | Zn = 9.7% |

Example 2

To a solution of 15.12 g of the zinc salt of formula (11) obtained in Example 1 in 110 ml of acetone are added 50 ml of an aqueous 1N hydrochloric acid solution. The acid solution is then kept for 1 hour at reflux temperature and subsequently concentrated by evaporation in vacuo. The residue is taken up in 80 ml of toluene, whereupon 2 phases form. The toluene phase is separated and concentrated by evaporation in vacuo, affording 13.1 g of a viscous product which is the salicylic acid compound of formula

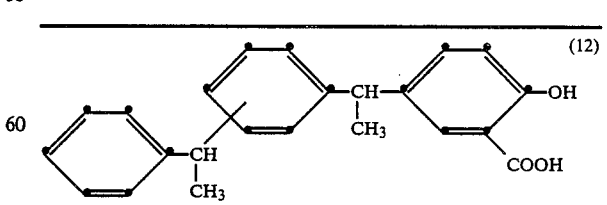

| | Elemental analysis: | |
|---|---|---|
| cal. | C = 79.74% | H = 6.4% |
| found | C = 80.6% | H = 6.8% |

Example 3

160 g of o-chlorotoluene are heated to 110° C. Then 3.65 g of 96% sulfuric acid are added dropwise over 35 minutes and the water formed is removed under reduced pressure. After cooling to 60° C., 125 g of 1-phenylethanol and 77.5 g of salicylic acid are added. The mixture is heated to 83° C. and the water formed during the condensation is continuously removed as an azeotrope under reduced pressure. The o-chlorotoluene is then distilled off and the residue is stirred in 560 ml of an aqueous 1N sodium hydroxide solution and then diluted with 1 liter of water. The resultant solution is left to stand for several hours at room temperature, after which time the oil that has formed on the surface is separated. The residual solution is then added dropwise at 10°–15° C. to a stirred solution of 47.7 g of zinc chloride in 300 ml of water. The precipitate is isolated by filtration, squeezed out, and the moist filter cake is suspended in 1 liter of water. The suspension is filtered and the filter cake is again squeezed out and then dried in vacuo at 100° C., affording 117 g of a powder with a melting range of about 135°–170° C. This product corresponds to the formula (11) in Example 1.

| Elemental analysis: | | | | |
|---|---|---|---|---|
| cal. | C = 73.06% | H = 5.6% | Zn = 8.64% | O = 12.69% |
| found | C = 71.8% | H = 5.7% | Zn = 8.54% | O = 12.35% |

Example 4

With stirring, 465 g of salicylic acid, 735 g of 1-phenylethanol and 36 g of p-toluenesulfonic acid.1H$_2$O are condensed for 3 hours at 120° C. The water formed during the condensation is continuously distilled off, with further distillation being effected for 30 minutes under reduced pressure after 3 hours. After cooling to 90° C., 1770 ml of an aqueous 2N sodium hydroxide solution are added and the resultant solution is then left to stand for several hours at room temperature. The oil that has formed on the surface is separated and the residual solution is then added at 10°–15° C. to a stirred solution of 290 g of zinc chloride in 4 liters of water. The white precipitate is isolated by filtration and squeezed out. The moist filter cake is suspended in 5 liters of water and the suspension is filtered. The filter cake is again squeezed out and then dried in vacuo at 50°–70° C., affording 965 g of a powder with a melting range of 105°–140° C. This product contains 95% of the zinc salicylate of the formula (11) of Example 1 and 5% of the zinc salicylate of the formula

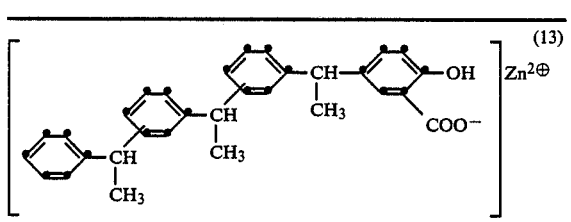

Elemental analysis:

| | | | | |
|---|---|---|---|---|
| cal. | C = 73.06% | H = 5.0% | Zn = 8.64% | O = 12.69% |
| found | C = 74.1% | H = 5.7% | Zn = 7.67% | O = 12.4% |

Example 5

With stirring, 77.5 g of salicylic acid, 125 g of 1-phenylthanol and 6 g of p-toluenesulfonic acid.2H$_2$O are condensed for 3 hours at 120° C. The water formed during the condensation is continuously distilled off, with further distillation being effected for 15 minutes under reduced pressure after 3 hours. After cooling to 90° C., 295 ml of an aqueous 2N sodium hydroxide solution are added and the resultant solution is then left to stand for several hours at room temperature. The oil that has formed on the surface is separated and the residual solution is then added at 10°–15° C. to a stirred solution of 36 g of Al$_2$(SO$_4$)$_3$.18H$_2$O in 200 ml of water. The white precipitate is isolated by filtration and squeezed out. The moist filter cake is suspended in 400 ml of water and the suspension is filtered. The filter cake is again squeezed out and then dried in vacuo at 50°–70° C., affording 149.5 g of a powder which is the aluminium salt of the formula

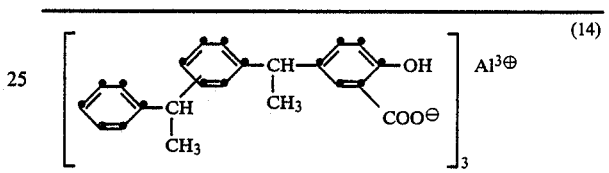

Elemental analysis:

| | | | | |
|---|---|---|---|---|
| cal. | C = 77.88% | H = 5.97% | Al = 2.53% | O = 13.54% |
| found | C = 77.6% | H = 6.15% | Al = 2.04% | O = 14.2% |

The product additionally contains 0.9% of H$_2$O.

Example 6

With stirring, 38.75 g of salicylic acid, 78.3 g of 1-(2'-chlorophenyl)ethanol and 3 g of p-toluenesulfonic acid.2H$_2$O are condensed for 3 hours at 120° C. The water formed during the condensation is continuously distilled off, with further distillation being effected for 15 minutes under reduced pressure after 3 hours. After cooling to 90° C., 147.5 ml of an aqueous 2N sodium hydroxide solution are added and the resultant solution is then left to stand for several hours at room temperature. The oil that has formed as lower phase is separated and the residual solution is then added at 10°–15° C. to an efficiently stirred solution of 24 g of zinc chloride in 200 ml of water. The precipitate is isolated by filtration and squeezed out. The moist filter cake is suspended in 400 ml of water and the suspension is filtered. The filter cake is again squeezed out and then dried in vacuo at 20° C., affording 70.4 g of a powder of the formula

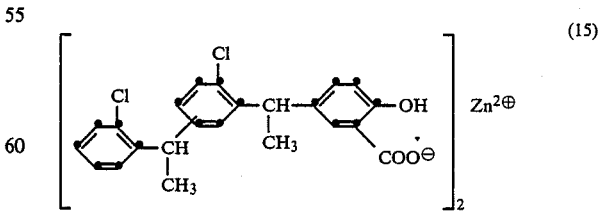

with a melting range of 84°–98° C.

| Elemental analysis: | | | | |
|---|---|---|---|---|
| cal. | C = 61.20% | H = 4.23% | Cl = 15.36% | Zn = 7.31% |

| Elemental analysis: | | | |
|---|---|---|---|
| found | C = 60.4% H = 4.23% | Cl = 15.82% | Zn = 7.11% |

Example 7

With stirring, 77.5 g of salicylic acid, 104.4 g of 1-(p-tolyl)ethanol and 6 g of p-toluenesulfonic acid.1H$_2$O are condensed for 3 hours at 120° C. The water formed during the condensation is continuously distilled off, with further distillation being effected for 15 minutes under reduced pressure after 3 hours. After cooling to 90° C., 295 ml of an aqueous 2N sodium hydroxide solution are added and the resultant solution is then left to stand for several hours at room temperature. The solid by-product that has formed on the surface is removed by filtration and the residual solution is then added at 10°–15° C. to an efficiently stirred solution of 50.3 g of zinc chloride in 400 ml of water. The precipitate is isolated by filtration and squeezed out. The moist filter cake is suspended in 400 ml of water and the suspension is filtered. The filter cake is again squeezed out and then dried in vacuo at 50°–70° C., affording 149.4 g of a powder of the formula

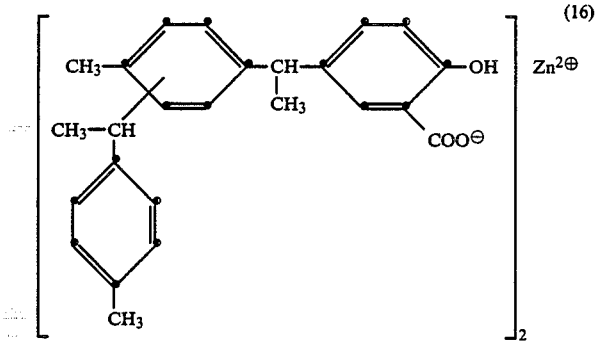

with a melting range of 100°–170° C.

USE EXAMPLES

Example 1

Pressure-sensitive recording system

A finely ground aqueous dispersion (2–4 μm) having a 38% solids content and comprising
1 part of the zinc salt of formula (11) obtained in Example 1,
13 parts of China clay
0.75 parts of a naphthalenesulfonic acid/formaldehyde condensate, and
1.5 parts of a styrene/butadiene copolymer (100%),
is applied with a doctor blade to coated paper having a weight of 48 g/m$^2$. Coating weight (dry): 6–7 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

Example 2

A finely ground aqueous dispersion (2–4 μm) having a 38% solids content and comprising
1 part of the aluminium salt of formula (14) obtained in Example 5,
6.5 parts of China clay
0.4 part of a naphthalenesulfonic acid/formaldehyde condensate, and
0.7 part of a styrene/butadiene copolymer (100%),
is applied with a doctor blade to coated paper having a weight of 48 g/m$^2$. Coating weight (dry): 4–6 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

Comparably good results are obtained by using the zinc salts of Examples 3, 4, 6 and 7 as colour formers instead of the aluminium salt of formula (14).

Example 3

Thermographic recording paper

Two dispersions A and B are first prepared. Dispersion A is prepared by grinding
8 g of the zinc salt of formula (11) prepared in Example (1),
28 g of a 10% aqueous solution of polyvinyl alcohol 25/140, and
24 g of water,
in a ball mill to a particle size of 2–4 μm, over 3 to 6 hours.

Dispersion B is prepared by grinding
1 g of crystal violet lactone,
3.5 g of a 10% aqueous solution of polyvinyl alcohol 25/140, and
4 g of water,
in a ball mill to a particle size of 2–4 μm.

The two dispersions are then mixed.

The colourless mixture is coated with a doctor blade on paper having a weight of 50 g/m$^2$. The coating weight of the mixture is 3 g/m$^3$ (dry weight). The thermographic recording paper so obtained has a colourless surface. A blue color develops rapidly at 125° C., with saturation being reached at 220° C.

Intense blue copies are also obtained by using the metal salicylates obtained in Examples 2 to 7.

Example 4

Thermotransfer (a) Preparation of an image transfer sheet A-1

A finely ground dispersion (2–4 μm) of the composition:
10 g of carnauba wax
20 g of crystal violet lactone
5 g of ethyl cellulose
100 g of water
is applied with a doctor blade to paper having a weight of 50 g/m$^2$. Coating weight: 7 g/m$^2$.

(b) Preparation of a receiver sheet B-1

A finely ground dispersion (2–4 μm) of the composition:
20 g of the zinc salt of Example 4
10 g of powdered silica
30 g of a 10% aqueous solution of polyvinyl alcohol
70 g of water
is applied with a doctor blade to paper having a weight of 50 g/m$^2$. Coating weight: 4–5 g/m$^2$.

The image transfer sheet A-1 is placed on the receiver sheet B-1, with the coated sides face to face. Heat is applied to the back of the image transfer sheet for 0.3 seconds by a thermoprinter, resulting in the formation of intense blue prints from 170° C. on the receiver sheet B-1.

Intense blue prints are also obtained by using the metal salts of Examples 1 to 3 and 5 to 7.

Example 5

Pressure-sensitive recording system

A finely ground aqueous dispersion (2–4 μm) having a 38% solids content and comprising
1 part of a mixture of the zinc salt of formula (11) obtained in Example 1, and the zinc salt of 3,5-bis(α-methylbenzyl)salicylic acid in the ratio 1:1,
7.4 parts of China clay
0.8 part of a naphthalenesulfonic acid/formaldehyde condensate, and
0.9 part of a styrene/butadiene copolymer (100%),
is applied with a doctor blade to coated paper having a weight of 48 g/m². Coating weight (dry)- 6–7 g/m².

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

What is claimed is:

1. A salicylic acid compound of the formula

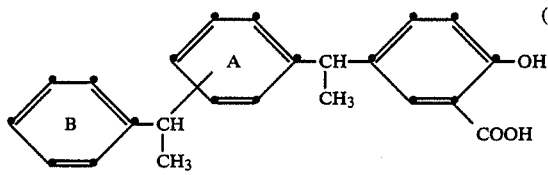

(3)

wherein each of the rings A and B independently of the other is unsubstituted or substituted by halogen, lower alkyl, lower alkoxy or an α-methylbenzyl radical.

2. A process for the preparation of a salicylic acid compound of the formula (3)

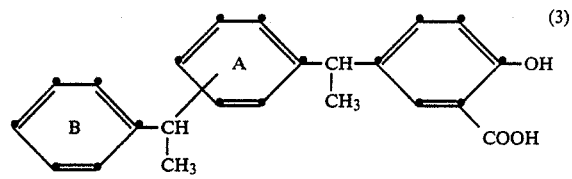

(3)

wherein each of the rings A and B independently of the other is unsubstituted or substituted by halogen, lower alkyl, lower alkoxy or an α-methylbenzyl radical, which comprises reacting 1 mole of salicylic acid with at least 1 mole of a 1-phenylethanol of the formula

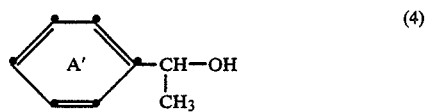

(4)

and at least 1 mole of a 1-phenylethanol of the formula

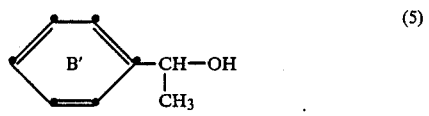

(5)

in the presence of an aromatic sulfonic acid, wherein in formulae (4) and (5) the rings A' and B' are unsubstituted or substituted by halogen, lower alkyl or lower alkoxy.

3. A process according to claim 2, wherein the reaction is carried out in the presence of p-toluenesulfonic acid.

4. A process according to claim 2, which comprises using an aromatic sulfonic acid which is prepared in situ.

5. A process according to claim 4, wherein the aromatic sulfonic prepared in situ is toluenesulfonic acid.

* * * * *